US011918764B2

(12) United States Patent
Soltis et al.

(10) Patent No.: US 11,918,764 B2
(45) Date of Patent: Mar. 5, 2024

(54) DIRECTIONAL ENHANCEMENT FEATURE FOR ARTICULATION CATHETER (71) Applicant: Boston Scientific Scimed Inc, Maple Grove, MN (US)

(72) Inventors: Brian Soltis, St Paul, MN (US); David Benjamin Joda, St Paul, MN (US); Raymond David Gessler, III, Roberts, WI (US); Seth Stomberg, Maple Lake, MN (US); Leonard Roldan Jimenez, St Paul, MN (US); Kyle Logan Lemke, St Paul, MN (US)

(73) Assignee: Boston Scientific Scimed, Inc., Maple Grove, MN (US)

( * ) Notice: Subject to any disclaimer, the term of this patent is extended or adjusted under 35 U.S.C. 154(b) by 384 days.

(21) Appl. No.: 17/179,663

(22) Filed: Feb. 19, 2021

(65) Prior Publication Data
US 2021/0260340 A1 Aug. 26, 2021

Related U.S. Application Data (60) Provisional application No. 62/979,826, filed on Feb. 21, 2020.

(51) Int. Cl.
*A61M 25/01* (2006.01)
*A61B 18/14* (2006.01)
*A61M 25/00* (2006.01)
*A61B 17/00* (2006.01)
*A61B 18/00* (2006.01)

(52) U.S. Cl.
CPC ..... *A61M 25/0147* (2013.01); *A61B 18/1492* (2013.01); *A61M 25/0026* (2013.01); *A61M 25/005* (2013.01); *A61B 2017/00292* (2013.01); *A61B 2018/00351* (2013.01); *A61B 2018/00577* (2013.01); *A61M 2205/0266* (2013.01)

(58) Field of Classification Search
None
See application file for complete search history.

(56) References Cited

U.S. PATENT DOCUMENTS

| | | | | | |
|---|---|---|---|---|---|
| 3,060,972 | A | * | 10/1962 | Sheldon | A61B 1/0055 138/120 |
| 3,521,620 | A | * | 7/1970 | Cook | A61M 25/09033 604/95.04 |
| 4,586,923 | A | * | 5/1986 | Gould | A61M 25/0147 604/95.04 |
| 4,934,340 | A | * | 6/1990 | Ebling | A61B 1/0058 600/117 |
| 5,231,989 | A | * | 8/1993 | Middleman | A61M 25/0147 604/95.01 |

(Continued)

Primary Examiner — Ryan J. Severson
(74) Attorney, Agent, or Firm — Nelson Mullins Riley & Scarborough LLP (57) ABSTRACT Various aspects of the present disclosure may be directed toward apparatuses, systems, and methods that include a medical device including an elongate body having a proximal portion, a distal portion, and three mutually perpendicular planes. The medical device may include a first steering line and a second steering line and a first stiffening material and a second stiffening material. The first stiffening material and the second stiffening material may be configured to maintain planarity of deflection of at least the distal portion of the elongate body.

20 Claims, 7 Drawing Sheets

(56) References Cited

U.S. PATENT DOCUMENTS

| | | | | |
|---|---|---|---|---|
| 5,368,564 | A | * | 11/1994 | Savage ............. A61M 25/0147 604/95.04 |
| 5,383,852 | A | * | 1/1995 | Stevens-Wright ........................... A61M 25/0141 604/95.04 |
| 5,571,085 | A | * | 11/1996 | Accisano, III .... A61M 25/0136 604/95.01 |
| 6,450,948 | B1 | * | 9/2002 | Matsuura ............. A61B 1/0055 606/1 |
| 8,725,228 | B2 | | 5/2014 | Koblish et al. |
| 10,293,137 | B2 | * | 5/2019 | Dale .................. A61M 25/0133 |
| 10,426,920 | B2 | | 10/2019 | Sutermeister et al. |
| 2009/0171348 | A1 | * | 7/2009 | Guo .................. A61M 25/0147 604/95.04 |
| 2016/0279386 | A1 | * | 9/2016 | Dale .................. A61M 25/0133 |
| 2019/0298969 | A1 | * | 10/2019 | Dale .................. A61M 25/0138 |
| 2021/0260340 | A1 | * | 8/2021 | Soltis ................ A61M 25/0147 |
| 2022/0111176 | A1 | * | 4/2022 | Dale .................... A61F 2/2427 |
| 2022/0193367 | A1 | * | 6/2022 | Joda .................. A61M 25/0147 |

\* cited by examiner

DIRECTIONAL ENHANCEMENT FEATURE FOR ARTICULATION CATHETER

This application claims priority to Provisional Application No. 62/979,826, filed Feb. 21, 2020, which is herein incorporated by reference in its entirety.

TECHNICAL FIELD

The present invention relates to medical devices and methods for catheters for accessing an anatomical space of the body. More specifically, the invention relates to devices and methods that include directional enhancement for catheters such as steerable catheters.

BACKGROUND

Various medical procedures involve catheters inserted into a patient's vasculature. In certain procedures, the catheter may be navigated through the vasculature to a target location in the body. The distal end of the catheters may be inserted into the patient's heart chambers in, for example, interventional electrophysiology procedures. The distal end of the catheter may include one or more electrodes that are used to delivery therapy (e.g., ablation) or map the surface of the heart tissue (e.g., identify the locations of heart tissue that are a source of the arrhythmias). Accurately locating and maintaining a location of the catheter, including the distal end portion of the catheter, may facilitate catheter performance.

SUMMARY

In Example 1, a medical device includes an elongate body having a proximal portion, a distal portion, and three mutually perpendicular planes, the elongate body being aligned with a first plane of the three mutually perpendicular planes; a first lumen aligned with the first plane and extending through the elongate body; a first steering line and a second steering line arranged on opposite sides of the first lumen relative to a second plane of the three mutually perpendicular planes and extending along the first plane of the three mutually perpendicular planes, the first steering line and the second steering line being configured to deflect at least the distal portion of the elongate body; and a first stiffening material and a second stiffening material spaced on opposite sides of the first lumen relative to a third plane of the three mutually perpendicular planes and extending along the first plane of the three mutually perpendicular planes, the first stiffening material and the second stiffening material being configured to maintain planarity of deflection of at least the distal portion of the elongate body.

In Example 2, further to the medical device of Example 1, the first stiffening material and the second stiffening material are arranged within the distal portion of the elongate body.

In Example 3, further to the medical device of any one of Examples 1-2, the first stiffening material and the second stiffening material are configured to maintain at least the distal portion of the elongate body substantially aligned with the third plane in response to the deflection.

In Example 4, further to the medical device of Example 3, the first stiffening material and the second stiffening material are configured to resist deflection of at least the distal portion of the elongate body out of the third plane.

In Example 5, further to the medical device of Example 4, the first stiffening material and the second stiffening material are configured to bias at least the distal portion of the elongate body to substantially align with the deflection.

In Example 6, further to the medical device of any one of Examples 1-5, the first stiffening material and the second stiffening material are configured to stabilize at least the distal portion of the elongate body.

In Example 7, further to the medical device of any one of Examples 1-6, further including a first lumen for the first steering line and a second lumen for the second steering line and diameters of the first lumen and the second lumen are greater than diameters of the first stiffening material and the second stiffening material.

In Example 8, further to the medical device of any one of Examples 1-7, wherein the elongate body includes an inner layer, a reinforcing braid, and an outer layer, and the first stiffening member and the second stiffening member are arranged within the inner layer and between about 0 mm and about 0.25 mm from the outer layer.

In Example 9, further to the medical device of any one of Examples 1-8, the first lumen is oval shaped, non-circular shaped, circular shape, or clover-leaf shaped.

In Example 10, further to the medical device of Example 9, the first lumen is a working channel through which one or more devices may be passed.

In Example 11, further to the medical device of any one of Examples 1-10, the first stiffening material is arranged about 90 degrees offset from the first steering line and the second stiffening material is arranged 90 degrees offset from the second steering line.

In Example 12, further to the medical device of any one of Examples 1-11, the first stiffening material and the second stiffening material each include at least one of a cable, wire, polymer fiber, coil of material, strips, and a braided material.

In Example 13, further to the medical device of any one of Examples 1-12, the first stiffening material and the second stiffening material each include at least one of Nitinol, stainless steel, and a polymer.

In Example 14, further to the medical device of any one of Examples 1-13, the first stiffening material and the second stiffening material are embedded within the elongate body.

In Example 15, further to the medical device of any one of Examples 1-14, the first stiffening material and the second stiffening material are configured to compress and maintain the planarity of deflection.

In Example 16, a medical device includes an elongate body having a proximal portion, a distal portion, and three mutually perpendicular planes, the elongate body being aligned with a first plane of the three mutually perpendicular planes; a first lumen aligned with the first plane and extending through the elongate body; a first steering line and a second steering line arranged on opposite sides of the first lumen relative to a second plane of the three mutually perpendicular planes and extending along the first plane of the three mutually perpendicular planes, the first steering line and the second steering line being configured to deflect at least the distal portion of the elongate body; and a first stiffening material and a second stiffening material spaced on opposite sides of the first lumen relative to a third plane of the three mutually perpendicular planes and extending along the first plane of the three mutually perpendicular planes, the first stiffening material and the second stiffening material being configured to bias at least the distal portion of the elongate body to substantially align with the deflection.

In Example 17, further to the medical device of Example 16, the first stiffening material and the second stiffening material are configured to maintain at least the distal portion of the elongate body substantially aligned with the third plane in response to the deflection.

In Example 18, further to the medical device of Example 17, the first stiffening material and the second stiffening material are configured to resist deflection of at least the distal portion of the elongate body out of the third plane.

In Example 19, further to the medical device of Example 18, the first stiffening material and the second stiffening material are configured to bias at least the distal portion of the elongate body to substantially align with the deflection.

In Example 20, further to the medical device of Example 19, the first stiffening material and the second stiffening material are configured to stabilize at least the distal portion of the elongate body.

In Example 21, further to the medical device of Example 16, further including a first lumen for the first steering line and a second lumen for the second steering line and diameters of the first lumen and the second lumen are greater than diameters of the first stiffening material and the second stiffening material.

In Example 22, further to the medical device of Example 16, the first stiffening material is arranged about 90 degrees offset from the first steering line and the second stiffening material is arranged 90 degrees offset from the second steering line.

In Example 23, further to the medical device of Example 16, the first stiffening material and the second stiffening material each include at least one of a cable, wire, polymer fiber, coil of material, and a braided material.

In Example 24, further to the medical device of Example 16, the first stiffening material and the second stiffening material each include at least one of Nitinol, stainless steel, and a polymer.

In Example 25, further to the medical device of Example 16, the first stiffening material and the second stiffening material are configured to compress and maintain the planarity of deflection.

In Example 26, a medical device includes an elongate body having a proximal portion, a distal portion, and mutually perpendicular planes, the elongate body being aligned with a first plane of the mutually perpendicular planes; a first lumen aligned with the first plane and extending through the elongate body; and a first stiffening material and a second stiffening material arranged on opposite sides of the first lumen relative to a second plane of the mutually perpendicular planes configured to maintain planarity of at least the distal portion of the elongate body in response to curvature of the elongate body.

In Example 27, further to the medical device of Example 26, the first stiffening material and the second stiffening material are arranged within the distal portion of the elongate body.

In Example 28, further to the medical device of Example 26, the elongate body includes an inner layer, a reinforcing braid, and an outer layer, and the first stiffening member and the second stiffening member are arranged within the inner layer and between about 0 mm and about 0.25 mm from the outer layer.

In Example 29, further to the medical device of Example 26, the first lumen is oval shaped and is a working channel through which one or more devices may be passed.

In Example 30, further to the medical device of Example 26, the first stiffening material and the second stiffening material are configured to compress and maintain the planarity of deflection.

In Example 31, a method of deflecting at least a portion of a medical device includes arranging an elongate body at a target location, the elongate body having a proximal portion, a distal portion, and three mutually perpendicular planes, the elongate body being aligned with a first plane of the three mutually perpendicular planes, a first lumen aligned with the first plane and extending through the elongate body, a first steering line and a second steering line arranged on opposite sides of the first lumen relative to a second plane of the three mutually perpendicular planes and extending along the first plane of the three mutually perpendicular planes, and a first stiffening material and a second stiffening material spaced on opposite sides of the first lumen relative to a third plane of the three mutually perpendicular planes and extending along the first plane of the three mutually perpendicular planes; and deflecting at least the distal portion of the elongate body using the first steering line and the second steering line while biasing at least the distal portion of the elongate body to substantially align with the deflection by the first stiffening material and the second stiffening material.

In Example 32, further to the method of Example 31, the first stiffening material and the second stiffening material are configured to maintain at least the distal portion of the elongate body substantially aligned with the second plane in response to the deflection.

In Example 33, further to the method of Example 32, the first stiffening material and the second stiffening material are configured to resist deflection of at least the distal portion of the elongate body out of the second plane.

In Example 34, further to the method of Example 33, the first stiffening material and the second stiffening material are configured to bias at least the distal portion of the elongate body to substantially align with the deflection.

In Example 35, further to the method of Example 34, the first stiffening material and the second stiffening material are configured to stabilize at least the distal portion of the elongate body.

While multiple embodiments are disclosed, still other embodiments of the present invention will become apparent to those skilled in the art from the following detailed description, which shows and describes illustrative embodiments of the invention. Accordingly, the drawings and detailed description are to be regarded as illustrative in nature and not restrictive.

While the invention is amenable to various modifications and alternative forms, specific embodiments have been shown by way of example in the drawings and are described in detail below. The intention, however, is not to limit the invention to the particular embodiments described. On the contrary, the invention is intended to cover all modifications, equivalents, and alternatives falling within the scope of the invention as defined by the appended claims.

DETAILED DESCRIPTION

Various aspects of the present disclosure are directed toward directional enhancement of catheters and steerable catheters. When arranged within a patient, catheters and steerable catheters may be steered or curved in a number of directions. The present disclosure includes aspects that facilitate and enhance directionality of the catheters and steerable catheters. As described in further detail below, at least portion of the catheters and steerable catheters may include directional enhancement features that bias the catheters and steerable catheters in a desired direction when curved.

Figure 1:
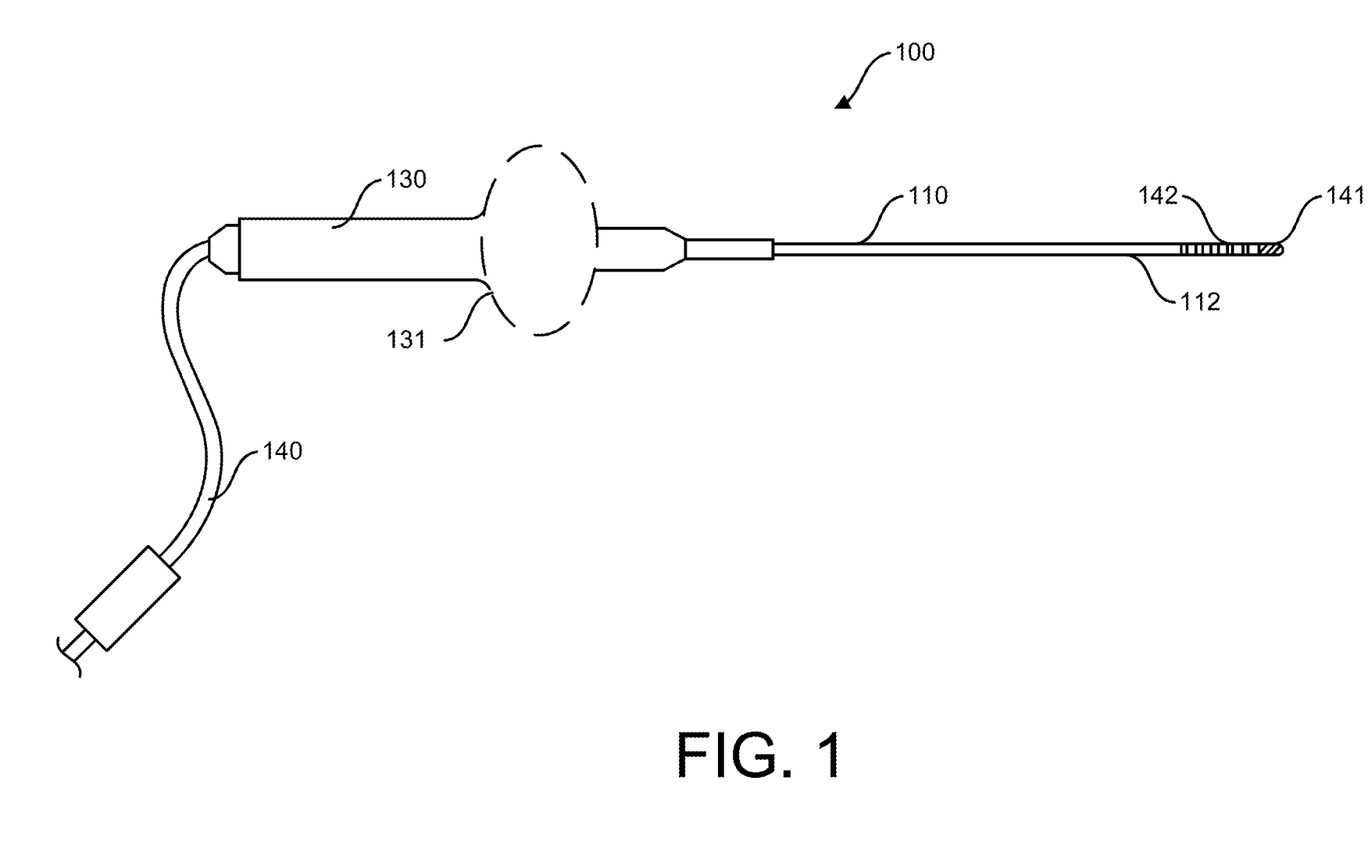
FIG. 1 is an illustration of an example catheter, consistent with various aspects of the present disclosure.
Figure 2:
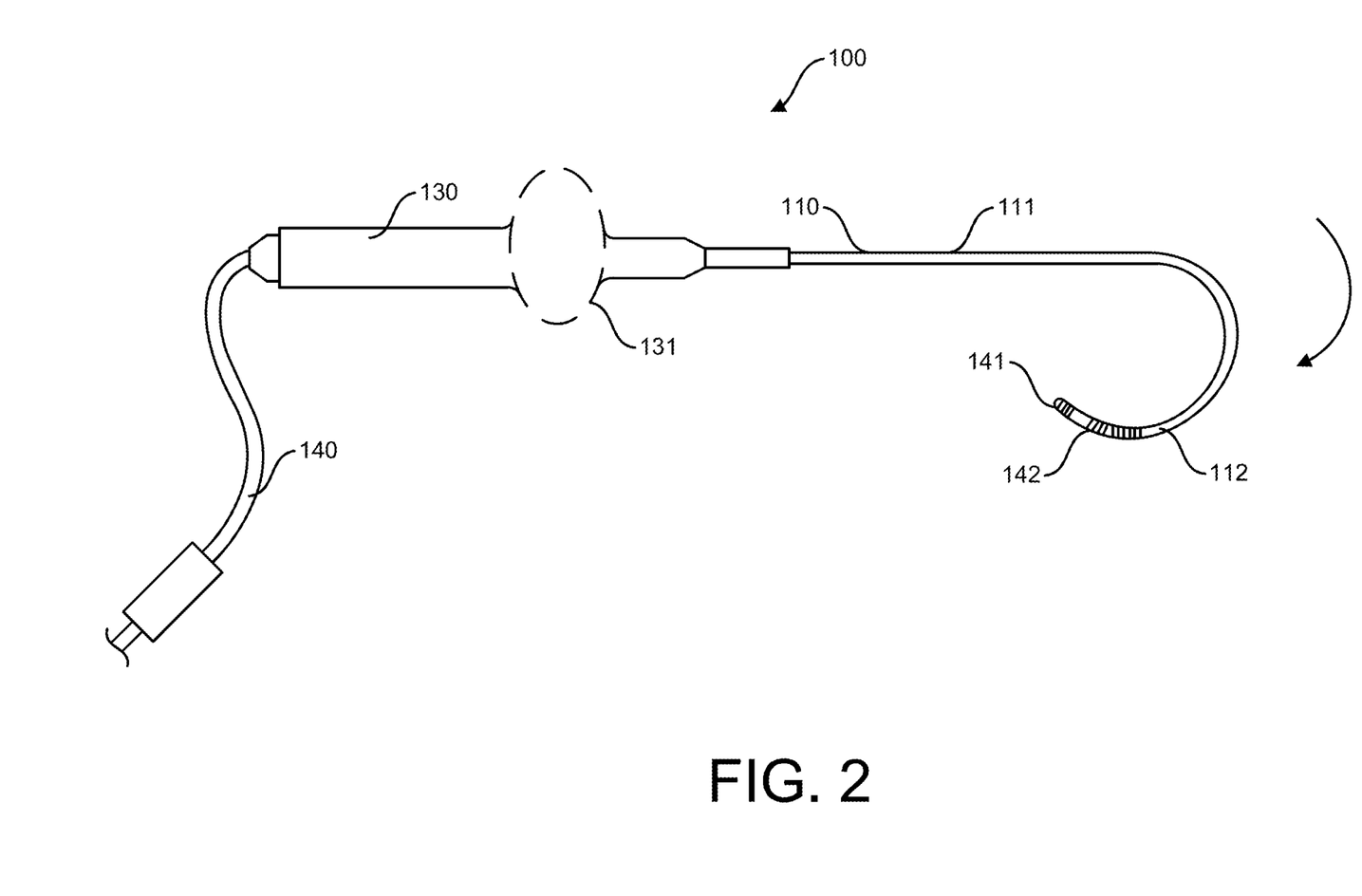
FIG. 2 is an illustration of the catheter, shown in FIG. 1, as deflected in a first direction, consistent with various aspects of the present disclosure.
Figure 3:
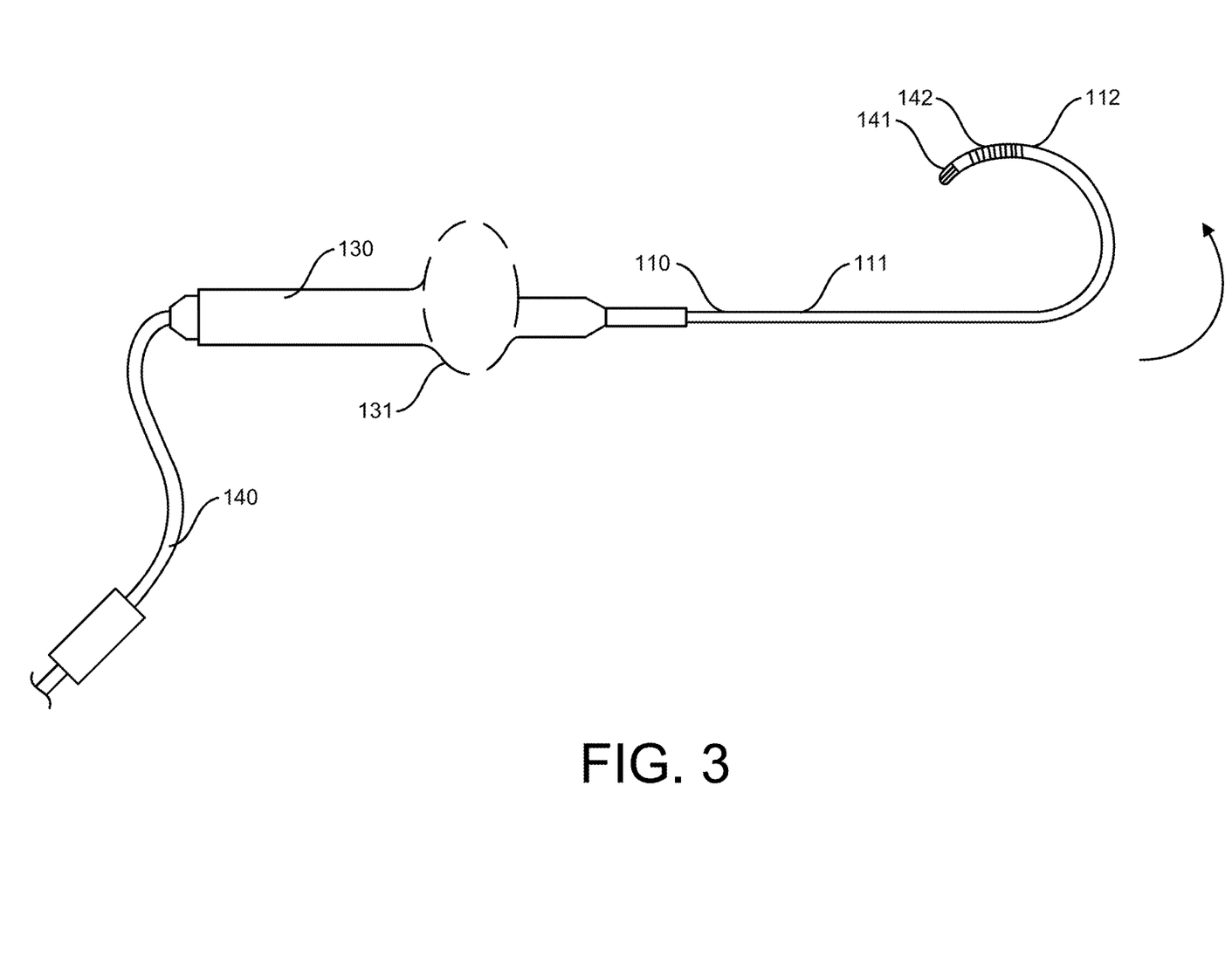
FIG. 3 is an illustration of the catheter, shown in FIGS. 1-2, as deflected in a second direction, consistent with various aspects of the present disclosure.

FIGS. 1-3 are illustrations of an example catheter, consistent with various aspects of the present disclosure. As shown in FIG. 1, the catheter 100 may be a steerable catheter 100. In certain instances, the catheter 100 is steerable in one direction (e.g., as shown in FIG. 2) or in multiple directions (as shown in FIGS. 2-3). The catheter 100 may include an elongate body 110 (e.g., a flexible shaft). In certain instances, the elongate body 110 extends from a distal portion of a handle 130. The elongate body 110 generally includes a proximal section or portion 111 and a steerable distal section or portion 112 that is sized and configured for placement and manipulation within in a target area of a heart of patient.

An electrical cable or other suitable connector 140 extending from a proximal end of the handle 130 may be coupled to a source of energy or other equipment (not shown in FIG. 1) for transmitting one or more ablation signals and/or receiving signals or data from mapping electrodes. FIG. 1 generally illustrates electrodes as a distal tip electrode 141 and shaft or ring electrodes 142.

Figure 5:
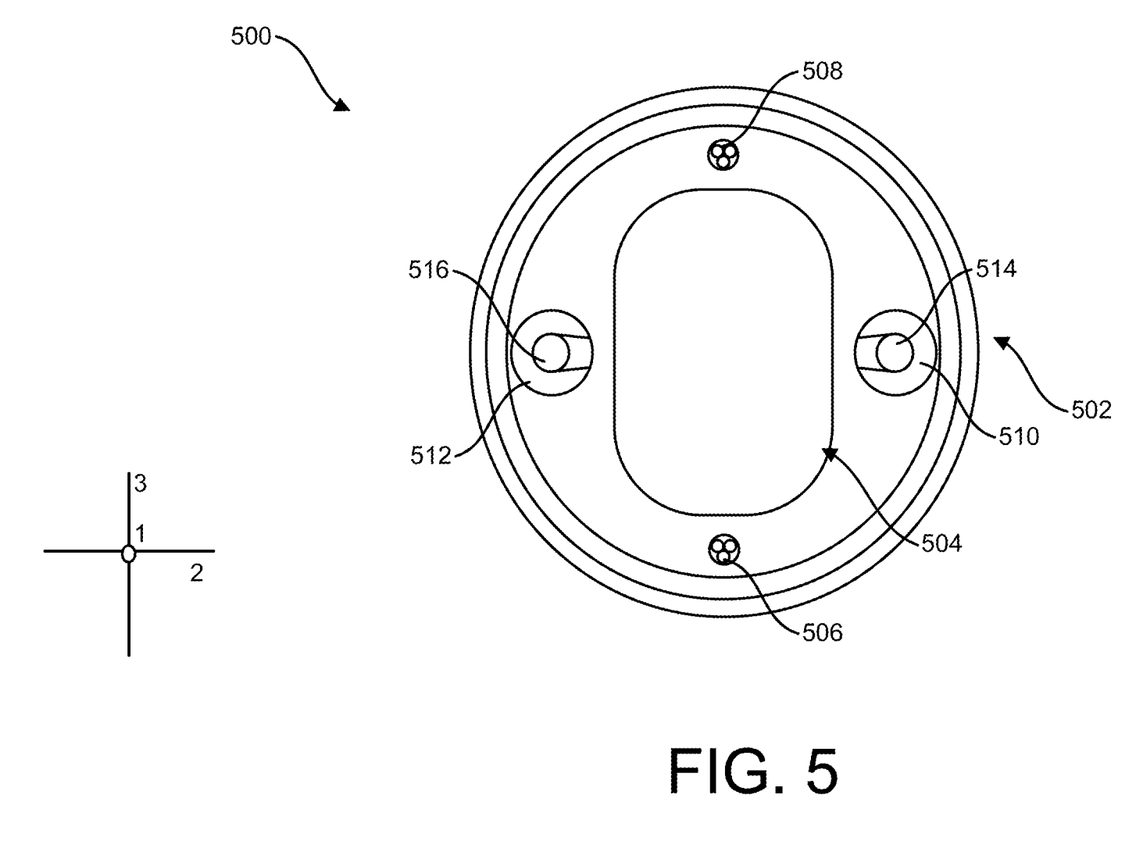
FIG. 5 is a cross-sectional illustration of an example catheter, consistent with various aspects of the present disclosure.

An actuator 131, such as a rotatable knob or plunger that may be arranged at a distal end of the handle 130, may be manipulated by the physician to deflect or position the distal section 112 of the elongate body 110 as desired by adjusting tension on one or more steering lines (e.g., as shown in FIG. 5).

As shown in FIGS. 2-3, during use, the elongate body 110 may be advanced into a patient and to a target location within the heart. After the catheter 100 is positioned, the actuator 131 may be used to deflect the distal section 112 to position the electrodes 141, 142 such that ablation and/or mapping may be performed. Deflecting or curving the distal section 112 may torque or twist the distal section 112 away from or out of the target location. The distal section 112 may torque out of plane from the plane in which the distal section 112 was arranged prior to deflection due to the tension on the steering lines and/or the curvature of the catheter 100 within vasculature. As discussed below, the catheter 100 may include directional enhancement features arranged with at least the distal section 112 such that the planarity of deflection the distal section 112 is maintained.

Figure 4:
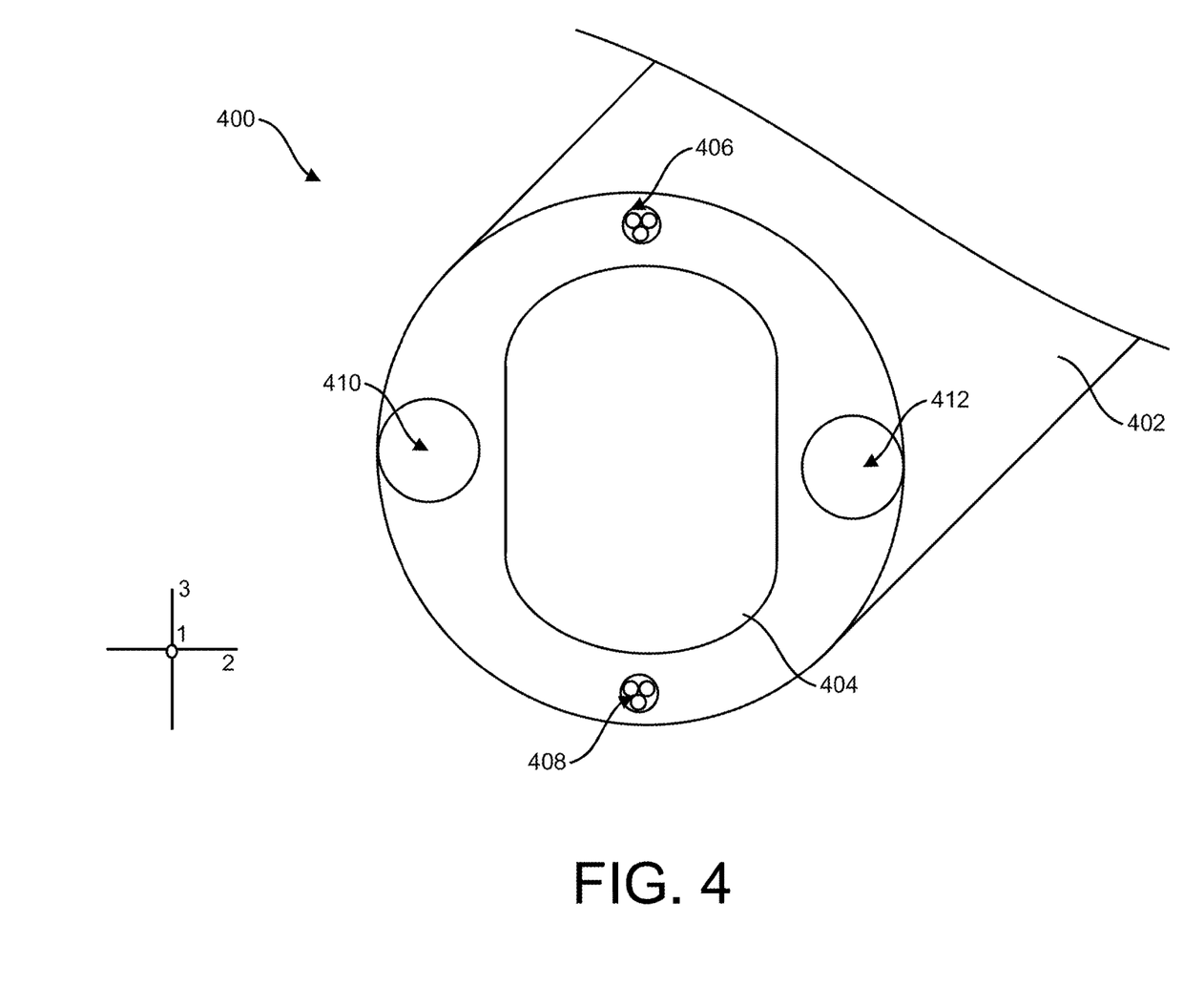
FIG. 4 is a cross-sectional illustration of an example catheter, consistent with various aspects of the present disclosure.

FIG. 4 is a cross-sectional illustration of an example catheter 400, consistent with various aspects of the present disclosure. The cross-section shown in FIG. 4 may be within a distal end portion of the catheter 400. The catheter 400, which may be steerable/deflectable as described above with reference to FIGS. 1-3, may include an elongate body 402. The elongate body 402 may include a proximal portion and a distal portion as shown above. In addition, the elongate body 402 may include mutually perpendicular planes (e.g., cartesian planes) with the elongate body 402 being aligned with a first plane or longitudinal axis of the mutually perpendicular planes. The mutually perpendicular planes are represented by the cartesian coordinate grid shown along with FIG. 4.

In certain instances, the catheter 400 also includes a first lumen 404 aligned with the first plane and extends through the elongate body 402. In certain instances, the first lumen 404 is a main or primary lumen of the catheter 400 and is arranged centrally within the elongate body 402. The catheter 400 may also include a first stiffening material 406 and a second stiffening material 408 arranged on a first side and a second opposite side of the first lumen 404. In certain instances, the first stiffening material 406 and the second stiffening material 408 may extend along the first plane and may be aligned with a third plane of the three mutually perpendicular planes. The elongate body 402 of the catheter 400 may be curved when arranged within a patient's vasculature. In certain instances, the curvature of the elongate body 402 may be relative to the second plane. The curvature may be intended by a physician to, for example, delivery therapy (e.g., ablation) or map the surface of the heart tissue (e.g., identify the locations of heart tissue that are a source of the arrhythmias).

Curvatures or deflections of the elongate body 402 may twist or torque out of approximately the second plane in certain instances. The first stiffening material 406 and the second stiffening material 408, however, are configured to maintain planarity of at least the distal portion of the elongate body 402 in response to curvature of the elongate body 402. The first stiffening material 406 and the second stiffening material 408 may stabilize at least the distal portion of the elongate body 402. For example, the first stiffening material 406 and the second stiffening material 408 may create a bias within at least the distal portion of the elongate body 402 and resist bending out of plane of at least the distal portion of the elongate body 402

In certain instances, as noted above, the catheter 400 may be steerable to deflect or curve the elongate body 402. The catheter 400 may also include a second lumen 410 and a third lumen 412 arranged on a third side and a fourth opposite side of the first lumen 404. In certain instances, the second lumen 410 and the third lumen 412 may extend along the first plane and may be aligned with a second plane of the three mutually perpendicular planes. In certain instances, a first steering line and a second steering line (as shown in FIG. 5) may be arranged within the first lumen and the second lumen. Thus, the first steering line and the second steering line may extend along the first plane and may be aligned with the second plane of the three mutually perpendicular planes. As described in further detail below, the first steering line and the second steering line are configured to deflect at least the distal portion of the elongate body 402. The first steering line and the second steering line may deflect the elongate body 402 relative to the second plane. In instances where the catheter 400 includes one or more steering lines, the first stiffening material 406 and the second stiffening material 408 are configured to maintain planarity of deflection of at least the distal portion of the elongate body 402. The first stiffening material 406 and the second stiffening material 408 are configured to maintain the elongate body 402 approximately within the third plane (e.g., within approximately +/−10% of the third plane) while the first steering line and the second steering line curve or deflect at least the distal portion of the elongate body 402 relative to the second plane.

FIG. 5 is a cross-sectional illustration of an example catheter 500, consistent with various aspects of the present disclosure. The cross-section shown in FIG. 4 may be within a distal end portion of the catheter 400. The catheter 500, which may be steerable/deflectable as described above with reference to FIGS. 1-3, may include an elongate body 502. The elongate body 502 may include a proximal portion and a distal portion as shown in FIGS. 1-3. The elongate body 402 is arranged relative to mutually perpendicular planes (e.g., cartesian planes) with the elongate body 402 being aligned with a first plane or longitudinal axis of the mutually perpendicular planes. The mutually perpendicular planes are represented by the cartesian coordinate grid shown along with FIG. 5.

The catheter 500 also includes a first lumen 504 aligned with the first plane and extends through the elongate body 502. The first lumen 504 may be a main or primary lumen of the catheter 500 and is arranged centrally within the elongate body 502. In certain instances, the first lumen 504 may include components such as one or more of wires for electrodes arranged along the distal portion of the elongate body 502 (e.g., as shown in FIGS. 1-3), navigational components, a temperature sensor (e.g., thermocouple), a force sensor, radio-frequency circuitry and/or wires, and a cooling lumen. The first lumen 506 may be a working channel through which one or more devices may be passed In certain instances, as noted above, the catheter 500 may be steerable to deflect or curve the elongate body 500. The catheter 500 may include a first steering wire lumen 510 and a second steering wire lumen 512 arranged on opposite side of the first lumen 504. A first steering line 514 and a second steering line 516 may be arranged within the first steering wire lumen 510 and the second steering wire lumen 512. The first steering line 514 and the second steering line 516 may be coupled to an actuator (as shown in FIGS. 1-3) at one end and to a distal portion of elongate body 502 at an opposite end. The first steering line 514 and the second steering line 516 may deflect or curve at least a distal portion of the elongate body 502 in response to tension on the first steering line 514 and the second steering line 516 applied by way of a physician manipulating the actuator.

In certain instances, the first steering line 514 and the second steering line 516 (as well as the first steering wire lumen 510 and the second steering wire lumen 512) may extend along the first plane and may be aligned with a second plane of the three mutually perpendicular planes. The first steering line 514 and the second steering line 516 are configured to deflect at least the distal portion of the elongate body 402. The first steering line 514 and the second steering line 516 may deflect the elongate body 502 relative to the second plane.

In certain instances, the first steering line 514 and the second steering line 516 may be formed using a suitable material that may be substantially flexible as well as has strength for torque control and limited stretch. Some suitable materials may include stainless steel, titanium, MP35N, a suitable alloy, and other suitable materials, such as, but not limited to, materials disclosed below.

The catheter 500 may also include a first stiffening material 506 and a second stiffening material 508 arranged on opposite sides of the first lumen 504. In certain instances, the first stiffening material 506 may be spaced apart 90 degrees relative to the first steering line 514 and the second steering line 516 and the second stiffening material 508 may be spaced apart 90 degrees relative to the first steering line 514 and the second steering line 516 as shown. In certain instances, the first stiffening material 506 and the second stiffening material 508 may extend along the first plane and may be aligned with a third plane of the three mutually perpendicular planes.

As noted above, the first steering line 514 and the second steering line 516 may deflect the elongate body 502 of the catheter 500 when arranged within a patient's vasculature. In certain instances, the deflection or curvature of the elongate body 502 may be relative to the second plane. The curvature may be intended by a physician to, for example, delivery therapy (e.g., ablation) or map the surface of the heart tissue (e.g., identify the locations of heart tissue that are a source of the arrhythmias).

Forces applied when the first steering line 514 and the second steering line 516 deflect the elongate body 502 may twist or torque the elongate body 502 out of approximately the second plane. The first stiffening material 506 and the second stiffening material 508 are configured to maintain planarity of at least the distal portion of the elongate body 502 in response to curvature of the elongate body 502. The first stiffening material 506 and the second stiffening material 508 may stabilize at least the distal portion of the elongate body 502. For example, the first stiffening material 506 and the second stiffening material 508 may create a bias at least the distal portion of the elongate body 502 to substantially align with the deflection. In certain instances, the first stiffening material 506 and the second stiffening material 508 resist bending out of approximately the third plane. The first stiffening material 506 and the second stiffening material 508 are configured to maintain the elongate body 502 approximately within the third plane (e.g., within approximately +/−10% of the third plane) while the first steering line 514 and the second steering line 516 curve or deflect at least the distal portion of the elongate body 502 relative to the second plane. In certain instances the first stiffening material 506 and the second stiffening material 508 are configured to maintain at least the distal portion of the elongate body 502 substantially aligned (e.g., within approximately +/−10%) with the third plane in response to the deflection In certain instances, the first steering line lumen 512 and the second steering line lumen 514 have diameters that are greater than diameters of the first stiffening material 506 and the second stiffening material 508. The medical device of first stiffening material 506 and the second stiffening material 508 may be stiffer than the elongate body 502. In certain instances, the first stiffening material 506 and the second stiffening material 508 may be one or a combination of a cable, wire, polymer fiber, coil of material, strips, or a braided material. The first stiffening member 610 and the second stiffening member 612 may be formed of the same or different materials. The first stiffening material 506 and the second stiffening material 508 may be formed of one or a combination of Nitinol, stainless steel, or a polymer (e.g., Pebax, Polyether ether ketone (PEEK), polyamides). The first stiffening material 506 and the second stiffening material 508 may force planarity of the elongate body 502 and lessen reliance of bending planarity on the relatively less stiff (e.g., polymer materials) of the elongate body 502. The first stiffening material 506 and the second stiffening material 508 may maintain curve shape of the elongate body 502 during deflection and maintain repeatability of achieving the curve shape of the elongate body 502 during deflection.

Figure 6A:
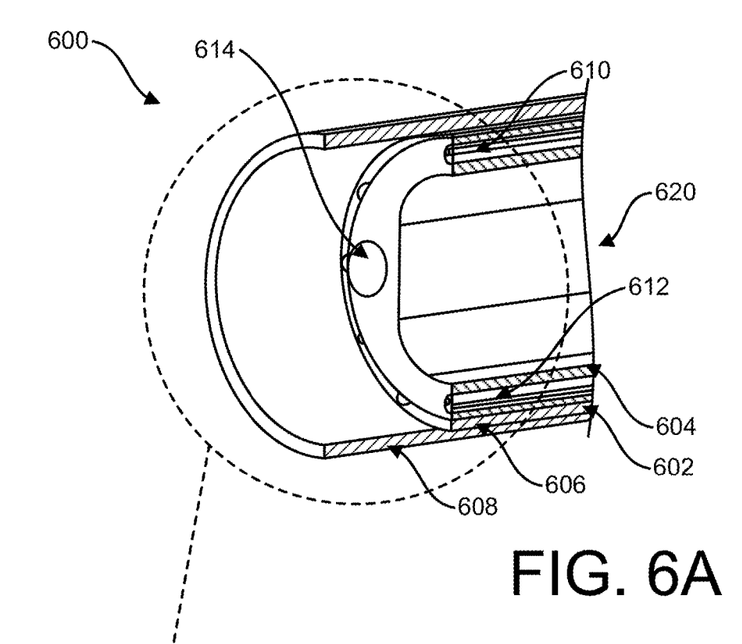
FIG. 6A is a cross-sectional illustration of a distal end portion of an example catheter, consistent with various aspects of the present disclosure.

FIG. 6A is a cross-sectional illustration of a distal end portion of an example catheter 600, consistent with various aspects of the present disclosure. The catheter 600 includes an elongate body 602 having an inner layer 604, a reinforcing braid 606, and an outer layer 608. In certain instances, lumens are formed in the inner layer 604 of the elongate body 602 as discussed in detail above. The inner layer 604, for example, may define a first lumen 620 extending along a length of the elongate body 602 and one or more steering wire lumens 614 that also may extend along the length of the elongate body 602. In certain instances, the reinforcing braid 606 may a plurality of interwoven wires that are woven, knitted, entwined, interlocked, or braided together. In some embodiments, the reinforcing braid 606 may form a web-like structure.

In certain instances, the catheter 600 includes a first stiffening member 610 and a second stiffening member 612. The first stiffening member 610 and the second stiffening member 612 may be embedded within the elongate body 602. In certain instances, the first stiffening member 610 and the second stiffening member 612 may be embedded within the inner layer 604 of the elongate body 602. In addition, the first stiffening member 610 and the second stiffening member 612 may be arranged within the inner layer 604 between about 0.0 mm and about 0.25 mm from the outer layer 608. In other instances, outer perimeters of the first stiffening member 610 and/or the second stiffening member 612 may be positioned with between about 5% and about 20% of a thickness of the inner layer 604 between the outer perimeters of the first stiffening member 610 and/or the second stiffening member 612 and the outer layer 608. The first stiffening member 610 and the second stiffening member 612 being arranged between about 0.005 mm and about 0.015 mm from the outer layer 608 may maximize a size of the first lumen 620. In certain instances, the first lumen 620 is oval in shape to maximize the size of the first lumen 620. In other instances, the first lumen 620 may be round, clover-leaf, non-circular, or other similar shapes to maximize the size of the first lumen 620.

Figure 6B:
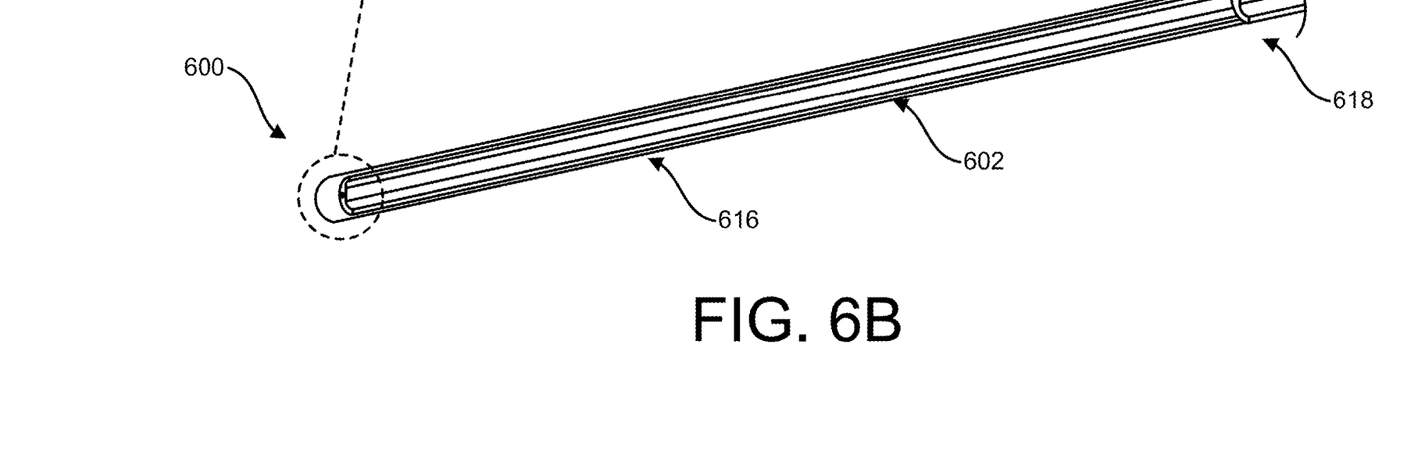
FIG. 6B is a cross-sectional illustration of a distal section the catheter, shown in FIG. 6A, consistent with various aspects of the present disclosure.

FIG. 6B is a cross-sectional illustration of a distal section 616 the catheter 600, shown in FIG. 6A, consistent with various aspects of the present disclosure. In certain instances, the first stiffening member 610 and the second stiffening member 612 are arranged within the distal section 616 (or portion) of the elongate body 602. The first stiffening member 610 and the second stiffening member 612 being arranged within the distal section 616 (or portion) of the elongate body 602 may stabilize at least the distal section 616 of the elongate body 602. In other instances, the first stiffening member 610 and the second stiffening member 612 may extend a length of the elongate body 602 or extend into an intermediate section 618 of the elongate body 602.

Figure 7:
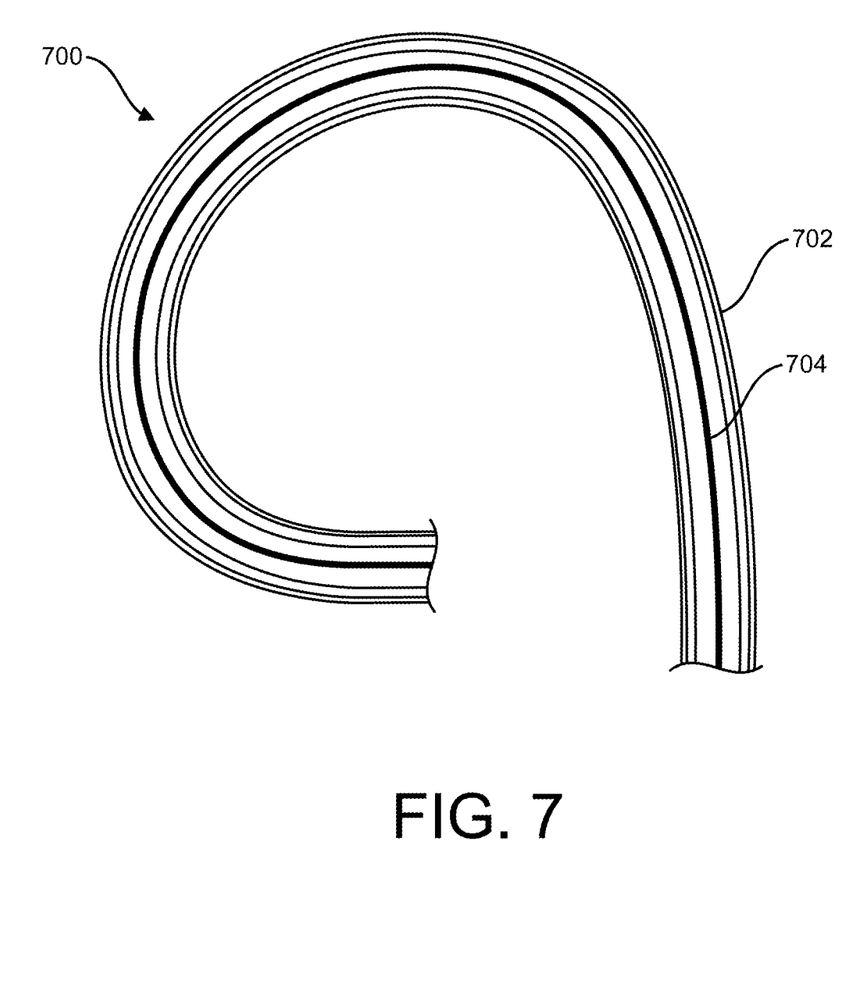
FIG. 7 is an illustration of a catheter as curved in-plane, consistent with various aspects of the present disclosure.

FIG. 7 is an illustration of a catheter 700 as curved in-plane, consistent with various aspects of the present disclosure. As discussed in detail above, the catheter 700 includes an elongate body 702 and one or more stiffening members 704 arranged within the elongate body 702. The stiffening members 704 facilitate maintaining planarity of the curvature of the elongate body 702. For example, the stiffening members 704 are configured to create a force perpendicular to the deflection (e.g., caused by steering lines) creating a bend between the stiffening members 704. The stiffening members 704 may be placed approximately 90 degrees from steering lines as shown in FIG. 5.

The stiffening members 704 facilitate in-plane steering of the elongate body 702 by forcing the elongate body 702 along a path of least resistance and curve directly with the steering lines. The stiffening members 704 maintain planarity by forcing the elongate body 702 to curve along a more flexible pathway due to the material of the elongate body 702 being of greater flexibility than the stiffening members 704. In certain instances, the stiffening members 704 (e.g., a first stiffening material and second stiffening material discussed above) may be compressed and maintain the planarity of deflection. The stiffening members 704 support lateral or in-plane movement of the elongate body 702 and lessen the movement (twisting or torqueing) of the elongate body 702 out of plane.

Various modifications and additions can be made to the exemplary embodiments discussed without departing from the scope of the present invention. For example, while the embodiments described above refer to particular features, the scope of this invention also includes embodiments having different combinations of features and embodiments that do not include all of the described features. Accordingly, the scope of the present invention is intended to embrace all such alternatives, modifications, and variations as fall within the scope of the claims, together with all equivalents thereof.

We claim:

1. A medical device, comprising:
    an elongate body having a proximal portion, a distal portion, and three mutually perpendicular planes, the elongate body being aligned with a first plane of the three mutually perpendicular planes;
    a first lumen aligned with the first plane and extending through the elongate body;
    a first steering line and a second steering line arranged on opposite sides of the first lumen relative to a second plane of the three mutually perpendicular planes and extending along the first plane of the three mutually perpendicular planes, the first steering line and the second steering line being configured to deflect at least the distal portion of the elongate body; and
    a first stiffening material and a second stiffening material spaced on opposite sides of the first lumen relative to a third plane of the three mutually perpendicular planes and extending along the first plane of the three mutually perpendicular planes, the first stiffening material and the second stiffening material being configured to bias at least the distal portion of the elongate body to substantially align with the deflection.

2. The medical device of claim 1, wherein the first stiffening material and the second stiffening material are configured to maintain at least the distal portion of the elongate body substantially aligned with the third plane in response to the deflection.

3. The medical device of claim 2, wherein the first stiffening material and the second stiffening material are configured to resist deflection of at least the distal portion of the elongate body out of the third plane.

4. The medical device of claim 3, wherein the first stiffening material and the second stiffening material are configured to bias at least the distal portion of the elongate body to substantially align with the deflection.

5. The medical device of claim 4, wherein the first stiffening material and the second stiffening material are configured to stabilize at least the distal portion of the elongate body.

6. The medical device of claim 1, further including a first lumen for the first steering line and a second lumen for the second steering line and diameters of the first lumen and the second lumen are greater than diameters of the first stiffening material and the second stiffening material.

7. The medical device of claim 1, wherein the first stiffening material is arranged about 90 degrees offset from the first steering line and the second stiffening material is arranged 90 degrees offset from the second steering line.

8. The medical device of claim 1, wherein the first stiffening material and the second stiffening material each include at least one of a cable, wire, polymer fiber, coil of material, and a braided material.

9. The medical device of claim 1, wherein the first stiffening material and the second stiffening material each include at least one of Nitinol, stainless steel, and a polymer.

10. The medical device of claim 1, wherein the first stiffening material and the second stiffening material are configured to compress and maintain the planarity of deflection.

11. A medical device, comprising:
an elongate body having a proximal portion, a distal portion, and mutually perpendicular planes, the elongate body being aligned with a first plane of the mutually perpendicular planes;
a first lumen aligned with the first plane and extending through the elongate body; and
a first stiffening material and a second stiffening material arranged on opposite sides of the first lumen relative to a second plane of the mutually perpendicular planes configured to maintain planarity of at least the distal portion of the elongate body in response to curvature of the elongate body.

12. The medical device of claim 11, wherein the first stiffening material and the second stiffening material are arranged within the distal portion of the elongate body.

13. The medical device of claim 11, wherein the elongate body includes an inner layer, a reinforcing braid, and an outer layer, and the first stiffening member and the second stiffening member are arranged within the inner layer and between about 0 mm and about 0.25 mm from the outer layer.

14. The medical device of claim 11, wherein the first lumen is oval shaped and is a working channel through which one or more devices may be passed.

15. The medical device of claim 11, wherein the first stiffening material and the second stiffening material are configured to compress and maintain the planarity of deflection.

16. A method of deflecting at least a portion of a medical device, the method comprising:
arranging an elongate body at a target location, the elongate body having a proximal portion, a distal portion, and three mutually perpendicular planes, the elongate body being aligned with a first plane of the three mutually perpendicular planes, a first lumen aligned with the first plane and extending through the elongate body, a first steering line and a second steering line arranged on opposite sides of the first lumen relative to a second plane of the three mutually perpendicular planes and extending along the first plane of the three mutually perpendicular planes, and a first stiffening material and a second stiffening material spaced on opposite sides of the first lumen relative to a third plane of the three mutually perpendicular planes and extending along the first plane of the three mutually perpendicular planes; and
deflecting at least the distal portion of the elongate body using the first steering line and the second steering line while biasing at least the distal portion of the elongate body to substantially align with the deflection by the first stiffening material and the second stiffening material.

17. The method of claim 16, wherein the first stiffening material and the second stiffening material are configured to maintain at least the distal portion of the elongate body substantially aligned with the second plane in response to the deflection.

18. The method of claim 17, wherein the first stiffening material and the second stiffening material are configured to resist deflection of at least the distal portion of the elongate body out of the second plane.

19. The method of claim 18, wherein the first stiffening material and the second stiffening material are configured to bias at least the distal portion of the elongate body to substantially align with the deflection.

20. The medical device of claim 19, wherein the first stiffening material and the second stiffening material are configured to stabilize at least the distal portion of the elongate body.

* * * * *